United States Patent
Osafune et al.

(10) Patent No.: US 9,902,938 B2
(45) Date of Patent: Feb. 27, 2018

(54) METHOD FOR INDUCING EXOCRINE PANCREATIC CELLS

(71) Applicant: Kyoto University, Kyoto-shi, Kyoto (JP)

(72) Inventors: Kenji Osafune, Kyoto (JP); Michinori Funato, Kyoto (JP); Norikazu Nishino, Kyoto (JP)

(73) Assignee: Kyoto University, Kyoto-shi, Kyoto (JP)

(*) Notice: Subject to any disclaimer, the term of this patent is extended or adjusted under 35 U.S.C. 154(b) by 11 days.

(21) Appl. No.: 14/655,482

(22) PCT Filed: Dec. 26, 2013

(86) PCT No.: PCT/JP2013/085334
§ 371 (c)(1),
(2) Date: Jun. 25, 2015

(87) PCT Pub. No.: WO2014/104403
PCT Pub. Date: Jul. 3, 2014

(65) Prior Publication Data
US 2016/0108366 A1    Apr. 21, 2016

Related U.S. Application Data

(60) Provisional application No. 61/745,945, filed on Dec. 26, 2012.

(51) Int. Cl.
*C12N 5/071* (2010.01)
*C12N 5/0735* (2010.01)

(52) U.S. Cl.
CPC ......... *C12N 5/0676* (2013.01); *C12N 5/0606* (2013.01); *C12N 2500/38* (2013.01); *C12N 2501/119* (2013.01); *C12N 2501/16* (2013.01); *C12N 2501/385* (2013.01); *C12N 2501/41* (2013.01); *C12N 2501/415* (2013.01); *C12N 2501/42* (2013.01); *C12N 2501/727* (2013.01); *C12N 2501/73* (2013.01); *C12N 2501/999* (2013.01); *C12N 2506/02* (2013.01)

(58) Field of Classification Search
CPC .......................... C12N 5/0676; C12N 5/0606
See application file for complete search history.

(56) References Cited

U.S. PATENT DOCUMENTS

2002/0151487 A1* 10/2002 Nickoloff ............. A61K 38/177
  514/19.6
2012/0122700 A1*  5/2012 Medveczky ........... C12Q 1/705
  506/2
2015/0133434 A1*  5/2015 Ott ....................... A61K 31/551
  514/220

OTHER PUBLICATIONS

Hardikar et al. PNAS 100(12):7117-7122, 2003.*
Bellman et al. J. Clin. Invest 95:2840-2845, 1995.*
Norikazu et al. Bioorganic & Medicinal Chemistry Letters 14:2427-2431, 2004.*
Heikkila and Akerman. Biochemical and Biophysical Research Communications 162(3):1207-1213, 1989, abstract.*
Nagai, Mika, et al., "Induction of Pancreatic Exocrine Cells Differentiated from ES Cells Using Low-Molecular-Weight Compound", Journal of the Japanese Society for Regenerative Medicine, 2011, vol. 10 Suppl, p. 194—with English Translation.
Chen, Shulbing, et al., "A Small Molecule that Directs Differentiation of Human ESCs Into the Pancreatic Lineage", Nature Chemical Biology, Apr. 2009, vol. 5, No. 4, pp. 258-265.
Kunisada, Yuya, et al., "Small Molecules Induce Efficient Differentiation into Insulin-Producing Cells from Human Induced Pluripotent Stem Cells", Stem Cell Research, 2012, vol. 8, pp. 274-284.
International Search Report based on International Application No. PCT/JP2013/085334, dated Apr. 15, 2014.
Written Opinion based on International Application No. PCT/JP2013/085334, dated Apr. 15, 2014.

* cited by examiner

*Primary Examiner* — Marcia S Noble
(74) *Attorney, Agent, or Firm* — McCarter & English, LLP

(57) ABSTRACT

An object of the present invention is to provide a method for inducing the differentiation of pancreatic precursor cells into exocrine pancreatic cells. The above object is achieved by providing a method for inducing the differentiation of pancreatic precursor cells into exocrine pancreatic cells using a culture solution containing a histone deacetylase inhibitor and/or a ligand protein for a Notch signal, and a protein kinase C activator.

25 Claims, 4 Drawing Sheets
(2 of 4 Drawing Sheet(s) Filed in Color)

Fig. 1

| Stage | Stage1 | Stage2 | | | Stage3 |
|---|---|---|---|---|---|
| Additive | •CHIR99021<br>•ActivinA | •FGF10<br>•KAAD-CYC | •FGF10<br>•KAAD-CYC<br>•RA | •FGF10<br>•ILV | •CHAP108<br>•ILV |
| Basal Medium | RPMI1640+B27 | DMEM+Glutamin+B27 | | | |
| Day | 6 days | 1 day | 2 days | 4 days | 4 or 8 days |

METHOD FOR INDUCING EXOCRINE PANCREATIC CELLS

RELATED APPLICATIONS

This application is a national stage application filed under 35 USC 371 of PCT/JP2013/085334, filed Dec. 26, 2013, which claims the benefit of U.S. Provisional patent application No. 61/745,945 filed Dec. 26, 2012, all of which are incorporated herein, in entirety, by reference.

TECHNICAL FIELD

The present invention relates to a method for inducing the differentiation of PDX1-positive pancreatic precursor cells into exocrine pancreatic cells. The present invention further relates to a method for inducing the differentiation of pluripotent stem cells into exocrine pancreatic cells, because PDX1-positive pancreatic precursor cells may be induced from pluripotent stem cells. The present invention further relates to a kit for inducing the differentiation of the aforementioned cells into exocrine pancreatic cells.

BACKGROUND ART

The pancreas is an organ having exocrine functions of secreting and sending pancreatic juice containing digestive enzymes into the alimentary canal and endocrine functions of secreting hormones such as insulin and glucagon into the blood. Endocrine depend on cell clusters scattered within the pancreas, referred to as islets of Langerhans. At least 95% of the pancreas is responsible for exocrine functions. The pancreatic juice secreted from exocrine pancreatic cells passes through the pancreatic duct and then travels to the duodenum via the duodenal papillary.

When inflammation continuously occurs in exocrine gland cells for a long period of time, the cells are gradually disrupted and then replaced by fibrous tissue, which induces chronic pancreatitis. Chronic pancreatitis is induced by pancreatic duct obstruction due to heavy alcohol consumption, gallstones, or the like, but may also be induced by unknown causes. Conservative therapy (e.g., the administration of a digestive enzyme drug) has been conducted for chronic pancreatitis. However, no basic therapeutic method has been established.

In recent years, pluripotent cells such as induced pluripotent stem cells (iPS cells), which are obtained by introducing an undifferentiated cell-specific gene into embryonic stem cells (ES cells) or somatic cells, have been reported. The elucidation of the cause of the aforementioned disease and the development of a therapeutic agent using tissue somatic cells obtained from such cells has been desired.

Pancreatic precursor cells capable of differentiating into endocrine cells and exocrine cells express PDX1. Hence, with the use of the PDX1 as a gene marker, a method for induction of pancreatic precursor cells from pluripotent stem cells has been developed (Chen S, et al., Nat Chem Biol. 2009, 5, 258-265). Many studies have been conducted concerning methods for inducing insulin-producing cells from the thus obtained pancreatic precursor cells. However, there have been few findings on differentiation-induction methods that are specialized for exocrine pancreatic cells.

SUMMARY OF INVENTION

Technical Problem

An objective of the present invention is to provide a novel method for inducing the differentiation of PDX1-positive pancreatic precursor cells into exocrine pancreatic cells. Another objective of the present invention is to provide, through combination with the method for inducing the differentiation of pluripotent stem cells into PDX1-positive pancreatic precursor cells, a method for efficiently inducing the differentiation of pluripotent stem cells into exocrine pancreatic cells.

Solution to Problem

As a result of intensive studies to achieve the above objectives, the present inventors have found that differentiation into exocrine pancreatic cells can be induced with high efficiency by culturing PDX1-positive pancreatic precursor cells in a medium containing a combination of a histone deacetylase inhibitor and/or a ligand protein for a Notch signal receptor, and a protein kinase C activator, and thus have completed the present invention.

The present invention encompasses the following [1] to [25].

[1] A method for producing exocrine pancreatic cells from PDX1-positive pancreatic precursor cells, comprising a step of culturing PDX1-positive pancreatic precursor cells in a culture solution supplemented with a histone deacetylase inhibitor and/or a ligand protein for a Notch signal receptor, and a protein kinase C activator.

[2] The method according to [1], wherein the histone deacetylase inhibitor is a compound having the structure of formula 1

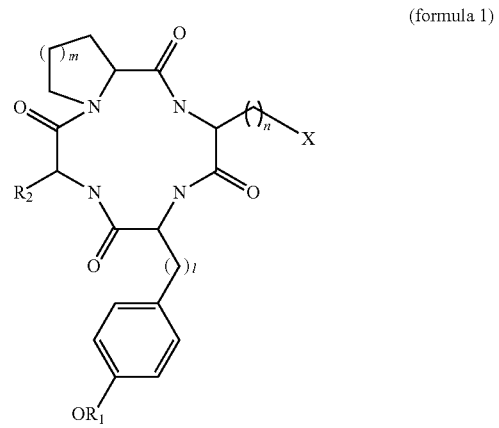

(formula 1)

(wherein, "l" represents 1 to 6, "m" represents 1 or 2, "n" represents 4 to 6, $R_1$ represents a $C_{1-6}$ alkyl group, $R_2$ represents a $C_{1-6}$ alkyl group, and X represents a substituent that is selected from the group consisting of the following formulae 2 to 9).

(formula 2)

(formula 3)

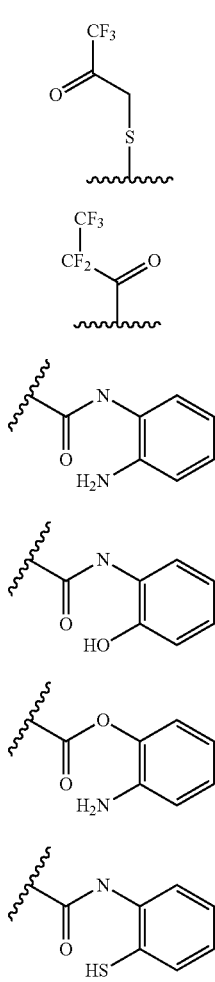

(formula 4)

(formula 5)

(formula 6)

(formula 7)

(formula 8)

(formula 9)

[3] The method according to [1] or [2], wherein the histone deacetylase inhibitor is a compound having the following structure of formula 10.

(formula 10)

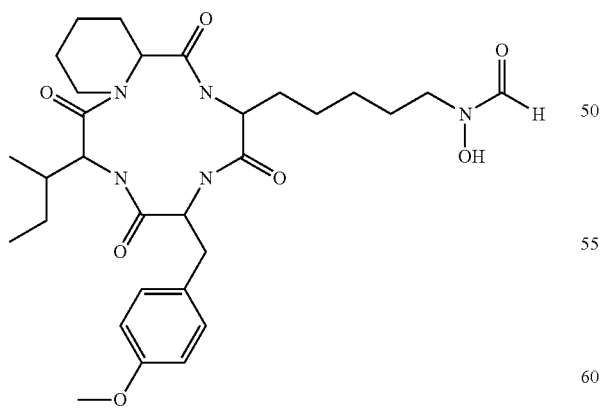

[4] The method according to any one of [1] to [3], wherein the ligand protein for the Notch signal receptor is DLL4 and/or JAG1.

[5] The method according to any one of [1] to [4], wherein the protein kinase C activator is indolactam V.

[6] The method according to any one of [1] to [5], wherein the step of culturing is performed for at least 2 days.

[7] The method according to any one of [1] to [6], wherein the PDX1-positive pancreatic precursor cells are PDX1-positive pancreatic precursor cells induced by the following steps (i) to (iv) from pluripotent stem cells:

(i) a step of culturing pluripotent stem cells in a culture solution supplemented with a GSK-3β inhibitor and activin A;

(ii) a step of culturing the cells obtained in (i) in a culture solution supplemented with FGF10 and an SMO inhibitor:

(iii) a step of culturing the cells obtained in (ii) in a culture solution supplemented with retinoic acid, FGF10, and an SMO inhibitor; and (iv) a step of culturing cells obtained in (iii) in a culture solution supplemented with a protein kinase C activator and FGF10.

[8] The method according to [7], wherein the GSK-3β inhibitor is CHIR99021.

[9] The method according to [7] or [8], wherein the SMO inhibitor is KAAD-cyclopamine.

[10] The method according to any one of [7] to [9], wherein the protein kinase C activator is indolactam V.

[11] The method according to any one of [7] to [10], wherein step (i) comprises dispersing pluripotent stem cells into single cells.

[12] The method according to any one of [7] to [11], wherein step (i) of culturing is performed for at least 4 days.

[13] The method according to any one of [7] to [12], wherein step (ii) of culturing is performed for at least 1 day.

[14] The method according to any one of [7] to [13], wherein step (iii) of culturing is performed for at least 2 days.

[15] The method according to any one of [7] to [14], wherein step (iv) of culturing is performed for at least 2 days.

[16] The method according to any one of [1] to [15], wherein the PDX1-positive pancreatic precursor cells are PDX1-positive human pancreatic precursor cells.

[17] Pancreatic precursor cells, which are produced by the method according to any one of [1] to [16].

[18] A kit for producing exocrine pancreatic cells from PDX1-positive pancreatic precursor cells, comprising a histone deacetylase inhibitor and/or a ligand protein for a Notch signal receptor, and a protein kinase C activator.

[19] The kit according to [18], wherein the histone deacetylase inhibitor is a compound having the structure of formula 11

(formula 11)

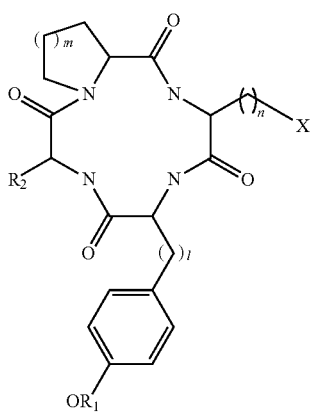

(wherein, "l" represents 1 to 6, "m" represents 1 or 2, "n" represents 4 to 6, $R_1$ represents a $C_{1-6}$ alkyl group, $R_2$ represents a $C_{1-6}$ alkyl group, and X represents any one of the substituents consisting of those represented by the following formulae 12 to 19).

(formula 12)
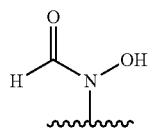

(formula 13)
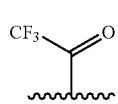

(formula 14)
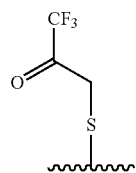

(formula 15)
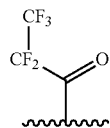

(formula 16)
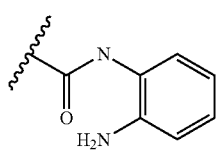

(formula 17)
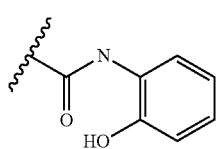

(formula 18)
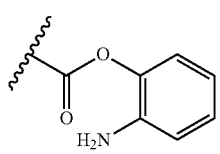

(formula 19)
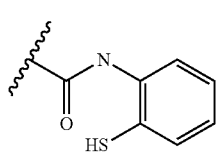

[20] The kit according to [18] or [19], wherein the histone deacetylase inhibitor is a compound having the structure represented by the following formula 20.

(formula 20)
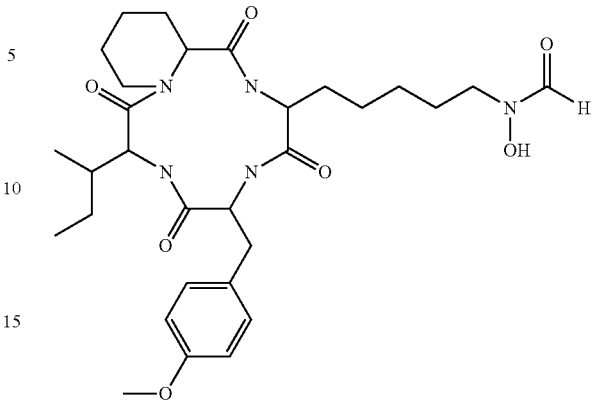

[21] The kit according to any one of [18] to [20], wherein the ligand protein for the Notch signal receptor is DLL4 and/or JAG1.

[22] The kit according to any one of [18] to [21], wherein the protein kinase C activator is indolactam V.

[23] A kit for producing exocrine pancreatic cells from pluripotent stem cells, further comprising a GSK-3β inhibitor, activinA, FGF10, and an SMO inhibitor in addition to the kit according to any one of [18] to [22].

[24] The kit according to [23], wherein the GSK-3β inhibitor is CHIR99021.

[25] The kit according to [23] or [24], wherein the SMO inhibitor is KAAD-cyclopamine.

Effects of the Invention

The method according to the present invention makes it possible to produce exocrine pancreatic cells from pancreatic precursor cells. Also, the use of the thus obtained exocrine pancreatic cells makes it possible to develop a therapeutic drug for a disease such as chronic pancreatitis.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 shows a scheme for producing exocrine pancreatic cells from pluripotent stem cells. In FIG. 1, KAAD-CYC denotes KAAD-cyclopamine, RA denotes retinoic acid, ILV denotes indolactam V, and CHAP108 denotes one of the histone deacetylase inhibitors.

In FIG. 3, blue denotes the images of nuclei stained with DAPI and green denotes the images resulting from staining with an anti-amylase antibody. DMSO denotes a negative control. At the top of FIG. 3, days measured after the addition of CHAP108, hDLL4, and hJAG1 are shown.

In FIG. 4, blue denotes the images of nuclei stained with DAPI and green denotes the images resulting from staining with an anti-amylase antibody. DMSO denotes a negative control. At the top of FIG. 4, days measured after the addition of CHAP108 (without ILV), ILV (without CHAP108) or CHAP108 and ILV are shown.

DESCRIPTION OF EMBODIMENTS

Figure 2:
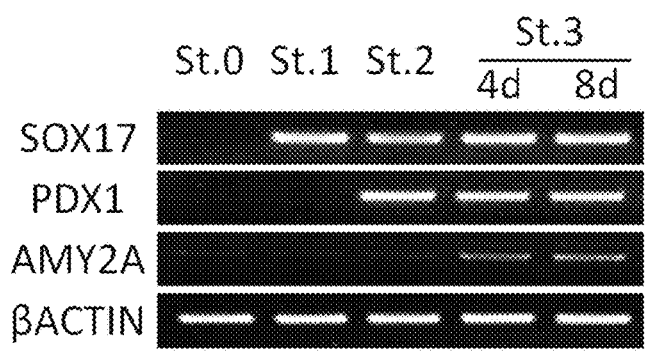
FIG. 2 shows the result of RT-PCR carried out for cells after each stage (St). The data shown for stage 3 were acquired after 4 days and after 8 days.

Hereinafter, the present invention will be described in detail.

The present invention provides a method for producing exocrine pancreatic cells from pancreatic precursor cells, comprising the step of culturing PDX1-positive pancreatic precursor cells in a culture solution supplemented with a histone deacetylase inhibitor and/or a ligand protein for a Notch signal receptor, and a protein kinase C activator.

In the present invention, the term "histone deacetylase inhibitor" is defined as a substance that inhibits the activity of histone deacetylase (HDAC). Examples thereof include, but are not limited to, a hydroxamic acid derivative, a cyclic tetrapeptide, a short-chain fatty acid (SCFA) derivative, a benzamide derivative, an electrophilic ketone derivative, and other HDAC inhibitors.

Examples of a hydroxamic acid derivative include, but are not limited to: suberoylanilide hydroxamic acid (SAHA) (Richon et al., Proc. Natl. Acad. Sci. U.S.A. 95, 3003-3007 (1998)); m-carboxy cinnamic acid bishydroxamide (CBHA) (Richon et al., supra); pyroxamide; trichostatin analogues such as trichostatin A (TSA) and trichostatin C (Koghe et al., Biochem. Pharmacol. 56: 1359-1364 (1998)); salicylohydroxamic acid (Andrews et al., International J. Parasitology 30, 761-768 (2000)); suberoyl bishydroxamic acid (SBHA) (U.S. Pat. No. 5,608,108); azelaic bishydroxamic acid (ABHA) (Andrews et al., supra); azelaic-1-hydroxamate-9-anilide (AAHA) (Qiu et al., Mol. Biol. Cell 11, 2069-2083 (2000)); 6-(3-chlorophenylureido)carpoic hydroxamic acid (3Cl-UCHA); oxamflatin [(2E)-5-[3-[(phenylsulfonyl)aminophenyl]-pent-2-en-4-ynohydroxamic acid] (Kim et al., Oncogene, 18: 2461-2470 (1999)); A-161906, Scriptaid (Su et al., Cancer Research, 60: 3137-3142(2000)); PXD-101(Prolifix); LAQ-824; CHAP; MW2796 (Andrews et al., supra); MW2996 (Andrews et al., supra); and any hydroxamic acid disclosed in U.S. Pat. Nos. 5,369,108, 5,932,616, 5,700,811, 6,087,367, and 6,511,990.

Examples of a cyclic tetrapeptide include, but are not limited to: a cyclic tetrapeptide having the structural formula of formula 1 (WO2004/113366 and Nishino N et al. Bioorganic & Medicinal Chemistry Letters, 14, 2427-2431, (2004)) such as trapoxin A (TPX)-cyclic tetrapeptide (cyclo-(L-phenylalanyl-L-phenylalanyl-D-pipecolinyl-L-2-amino-8-oxo-9,10-epoxyde canoyl)) (Kijima et al., J Biol. Chem. 268, 22429-22435 (1993)); FR901228 (FK 228, depsipeptide) (Nakajima et al., Ex. Cell Res. 241, 126-133 (1998)); FR225497 cyclic tetrapeptide (H. Mori et al., WO 00/08048 (17 Feb. 2000)); apicidin cyclic tetrapeptide [cyclo(N—O-mehyl-L-tryptophanyl-L-isoleucinyl-D-pipecolinyl-L-2-amino-8-oxodecanoyl)] (Darkin-Rattray et al., Proc. Natl. Acad. Sci. U.S.A. 93, 13143-13147 (1996)); apicidin Ia, apicidin Ib, apicidin Ic, apicidin IIa, and apicidin IIb (P. Dulski et al., WO 97/11366); CHAP, HC-toxin cyclic tetrapeptide (Bosch et al., Plant Cell 7, 1941-1950 (1995)); WF27082 cyclic tetrapeptide (WO 98/48825); and chlamydocin (Bosch et al., supra).

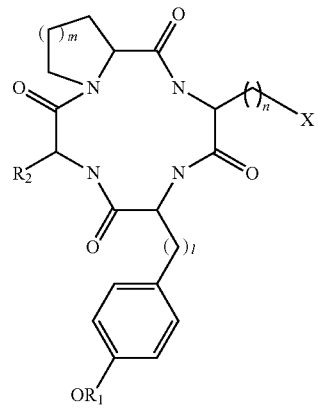
(formula 1)

A preferable example of a cyclic tetrapeptide is a compound of formula 1, wherein "l" represents 1 to 6, "m" represents 1 or 2, "n" represents 4 to 6, $R_1$, represents a $C_{1-6}$ alkyl group, $R_2$ represents a $C_{1-6}$ alkyl group, and X represents a substituent that is selected from the group consisting of those represented by the following formulae 2 to 9. Here, the term "$C_{1-6}$ alkyl group" refers to a linear, branched, or cyclic alkyl group. Examples thereof include a methyl group, an ethyl group, an n-propyl group, an isopropyl group, a cyclopropyl group, an n-butyl group, an isobutyl group, a sec-butyl group, a tert-butyl group, a cyclobutyl group, an n-pentyl group, an isopentyl group, a neopentyl group, a tert-pentyl group, a cyclopentyl group, n-hexyl group, a 2,2-dimethylbutyl group, a 3,3-dimethylbutyl group, a 2-ethyl butyl group, and a cyclohexyl group.

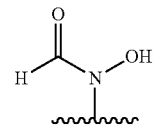
(formula 2)

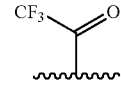
(formula 3)

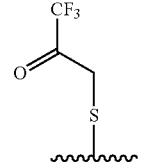
(formula 4)

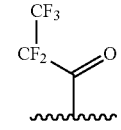
(formula 5)

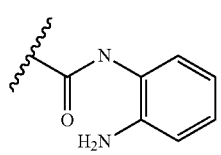
(formula 6)

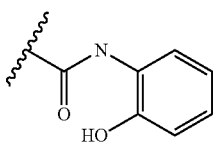
(formula 7)

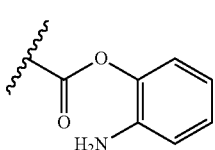
(formula 8)

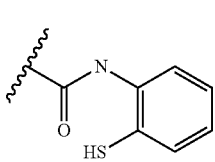
(formula 9)

More preferable examples of a cyclic tetrapeptide include compounds referred to as CHAP108 having the structure of formula 10.

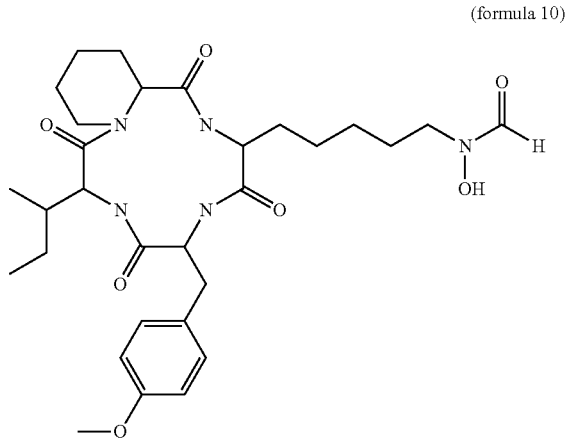 [SMILES: CCC(C)C1NC(=O)C(Cc2ccc(OC)cc2)NC(=O)C(CCCCCN(O)C=O)NC(=O)C2CCCCN2C1=O]
(formula 10)

Examples of a short-chain fatty acid (SCFA) derivative include, but are not limited to: sodium butyrate (NaB) (Cousens et al., J. Biol. Chem. 254, 1716-1723 (1979)); isovalerate (McBain et al., Biochem. Pharm. 53: 1357-1368 (1997)); valerate (McBain et al., supra); 4-phenylbutyrate (4-PBA) (Lea and Tulsyan, Anticancer Research, 15, 879-873 (1995)); phenylbutyrate (PB) (Wang et al., Cancer Research, 59, 2766-2799 (1999)); propionate (McBain et al., supra); butyl amide (Lea and Tulsyan, supra); isobutyl amide (Lea and Tulsyan, supra); phenylacetate (Lea and Tulsyan, supra); 3-bromopropionate (Lea and Tulsyan, supra); tributyrin (Guan et al., Cancer Research, 60, 749-755 (2000)); and valproic acid, valproate, and Pivanex (trademark).

Examples of a benzamide derivative include, but are not limited to: CI-994; MS-275 [N-(2-aminophenyl)-4-[N-(pyridine-3-ylmethoxycarbonyl)aminomethyl]benzamide] (Saito et al., Proc. Natl. Acad. Sci. U.S.A. 96, 4592-4597 (1999)); and a 3'-amino derivative of MS-275 (Saito et al., supra).

Examples of an electrophilic ketone derivative include, but are not limited to, trifluoromethyl ketone (Frey et al, Bioorganic & Med. Chem. Lett., 12, 3443-3447 (2002): U.S. Pat. No. 6,511,990) and α-ketoamide such as N-methyl-α-ketoamide.

Examples of other HDAC inhibitors include, but are not limited to, natural products, psammaplin, and depudecin (Kwon et al., PNAS 95: 3356-3361 (1998)).

Furthermore, in the present invention, the term "Notch signal receptor" refers to a single transmembrane protein, and specifically a hetero dimer comprising Notch extracellular domain (NECD) and TM-NICD that results from processing (cutting) of a Notch receptor comprising NECD, a transmembrane domain (TM) and NICD into TM-NICD. Examples of a ligand for the Notch signal receptor include members of the Delta-like family (DLL1, DLL3, DLL4) and members of the Jagged family (JAG1, JAG2). A ligand for the Notch signal receptor may be a recombinant that is marketed from Adipogen, for example, which can be easily used. Such a ligand for the Notch signal receptor to be used in the present invention is preferably DLL4 or JAG1.

Furthermore, in the present invention, the term "protein kinase C activator" is defined as a substance that activates protein kinase C (PKC). Examples thereof include, but are not limited to, diterpene (e.g., phorbolester), indole alkaloid (e.g., teleocidin, lyngbyatoxin, and indolactam V), polyacetate (e.g., aplysiatoxin and oscillatoxin), a certain derivative of diaminobenzyl alcohol (2S,5S)-(E,E)-8-(5-(4-(Trifluoromethyl)phenyl)-2,4-pentadiemoylamino)benzolactam (TPB) and bryostatin. The PKC activator to be used in the present invention is preferably indolactam V.

Furthermore, in the present invention, the term "pancreatic precursor cells" refers to cells that can differentiate into 3 types of cells, endocrine cells, exocrine cells, and duct cells, and express PDX1 and SOX17. In the present invention, PDX1 has the nucleic acid sequence shown in the NCBI accession No. NM_000209, in the case of humans. Similarly, SOX17 has the nucleic acid sequence shown in NM_022454.

Furthermore, in the present invention, the term "exocrine pancreatic cells" refers to, but is not particularly limited to, cells that secrete digestive enzymes such as trypsin, chymotrypsinogen, amylase, and lipase, and preferably cells that express the mRNA of amylase within the cells. The mRNA of amylase is AMY2A or AMY2B in the case of humans, each of which has the nucleic acid sequence shown in NCBI accession No. NM_000699 or NM_020978.

In the present invention, a culture solution to be used for inducing the differentiation of pancreatic precursor cells into exocrine pancreatic cells can be prepared using a medium for culturing animal cells, as a basal medium. Example of a basal medium include IMDM, Medium 199, Eagle's Minimum Essential Medium (EMEM), αMEM, Dulbecco's modified Eagle's Medium (DMEM), Ham's F12 medium, an RPMI 1640 medium, Fischer's medium, and mixtures thereof. A preferable example thereof is an RPMI 1640 medium. A medium may contain serum or may be serum-free. If necessary, a medium can contain: one or more serum substitutes, such as albumin, transferrin, Knockout Serum Replacement (KSR) (a serum substitute for FBS upon the culture of ES cells), N2 supplement (Invitrogen), B27 supplement (Invitrogen), a fatty acid, insulin, a collagen precursor, a trace element, 2-mercaptoethanol, and 3'-thiolglycerol; and one or more substances such as a lipid, an amino acid, L-glutamine, Glutamax (Invitrogen), a nonessential amino acid, a vitamin, a growth factor, a low molecular weight compound, an antibiotic, an antioxidant, a pyruvic acid, a buffering agent, and inorganic salts. A preferable medium is DMEM containing B27 supplement and L-glutamine.

Furthermore, cells may be cultured using a coated culture dish. Examples of a coating agent include matrigel (BD), collagen, gelatin, laminin, heparan sulfate proteoglycan, entactin, and combinations thereof. A preferable example thereof is matrigel.

The culture period is not particularly limited and is at least 2 days. Since long-term culture causes no special problem, two or more days for culturing can be adequately selected. Examples of days for culturing include 2, 3, 4, 5, 6, 7, 8, 9, 10, 11, 12 days, or more days.

Regarding the concentrations of the above substances to be added, persons skilled in the art can adequately select and use a concentration depending on efficacy. When CHAP108 (formula 10) is selected as a histone deacetylase inhibitor, the concentration thereof generally ranges from 100 nM to 10 µM, such as 100 nM, 200 nM, 300 nM, 400 nM, 500 nM, 1 µM, 2 µM, 3 µM, 4 µM, 5 µM or 10 µM. Similarly, a ligand protein for a Notch signal receptor may be added at the concentration that can induce HES1 expression within cells to a culture solution. When DLL4 or JAG1 is selected, the concentration thereof generally ranges from 1 µg/ml to 100 µg/ml such as 1 µg/ml, 2 µg/ml, 3 µg/ml, 4 µg/ml, 5 µg/ml, 10 µg/ml, 20 µg/ml, 30 µg/ml, 40 µg/ml, 50 µg/ml or 100 µg/ml. Similarly, when indolactam V is selected as a protein kinase C activator, the concentration thereof generally ranges from 100 nM to 1 µM such as 100 nM, 200 nM, 300 nM, 400 nM, 500 nM, 600 nM, 700 nM, 800 nM, 900 nM and 1 µM.

In the present invention, pancreatic precursor cells may be those isolated from a living body, or those induced in vitro from another cell species, and are preferably cells induced from pluripotent stem cells.

<Pluripotent Stem Cells>

Pluripotent stem cells that can be used in the present invention are stem cells having both pluripotency, by which the cells are capable of differentiating into all cells existing in vivo, and, proliferation potency. Examples of these pluripotent stem cells include embryonic stem (ES) cells, embryonic stem (ntES) cells derived from clone embryos obtained by nuclear transplantation, spermatogonial stem (GS) cells, embryonic germ (EG) cells, induced pluripotent stem (iPS) cells, pluripotent cells derived from cultured fibroblasts and myeloid stem cells (Muse cells). In the present invention, it is preferable to use iPS cells or Muse cells since these cells can be obtained without disruption of embryos.

(A) Embryonic Stem Cells

ES cells are stem cells having pluripotency and proliferation potency via self-replication, which are established from inner cell mass of early embryos (e.g., blastocysts) of a mammal such as a human or a mouse.

ES cells are stem cells from embryos originated from inner cell mass of blastocysts that are embryos after the 8-cell stage of fertilized eggs and the morula stage. ES cells have so-called pluripotency, by which they are capable of differentiating into all cells composing an adult, and proliferation potency via self-replication. ES cells were discovered in mice in 1981 (M. J. Evans and M. H. Kaufman (1981), Nature 292: 154-156). Thereafter, ES cell lines were established in primates including humans, monkeys, and the like (J. A. Thomson et al. (1999), Science 282: 1145-1147; J. A. Thomson et al. (1995), Proc. Natl. Acad. Sci. U.S.A., 92: 7844-7848; J. A. Thomson et al. (1996), Biol. Reprod., 55: 254-259; J. A. Thomson and V. S. Marshall (1998), Curr. Top. Dev. Biol., 38: 133-165).

ES cells can be established by removing inner cell mass from blastocysts of fertilized eggs of a subject animal and then culturing the inner cell mass on fibroblasts as feeders. Also, cell maintenance by subculture can be carried out using a culture solution supplemented with substances such as a leukemia inhibitory factor (LIF) and a basic fibroblast growth factor (bFGF). Methods for establishment and maintenance of human and monkey ES cells are described in U.S. Pat. No. 5,843,780; Thomson J A, et al. (1995), Proc Natl. Acad. Sci. U.S.A., 92: 7844-7848; Thomson J A, et al., (1998), Science. 282: 1145-1147; H. Suemori et al. (2006), Biochem. Biophys. Res. Commun., 345: 926-932; M. Ueno et al. (2006), Proc. Natl. Acad. Sci. U.S.A., 103: 9554-9559; H. Suemori et al. (2001), Dev. Dyn., 222: 273-279; H. Kawasaki et al. (2002), Proc. Natl. Acad. Sci. U.S.A., 99: 1580-1585; Klimanskaya I, et al. (2006), Nature. 444: 481-485, for example.

As a culture solution for preparation of ES cells, a DMEM/F-12 culture solution supplemented with 0.1 mM 2-mercaptoethanol, 0.1 mM nonessential amino acid, 2 mM L-glutamic acid, 20% KSR, and 4 ng/ml b-FGF is used, for example. Human ES cells can be maintained under wet atmosphere of 5% $CO_2$/95% air at 37° C. (O. Fumitaka et al. (2008), Nat. Biotechnol., 26: 215-224). Also, it is necessary for ES cells to subculture every 3 to 4 days. At this time, subculture can be carried out using 0.25% trypsin and 0.1 mg/ml collagenase IV in PBS containing 1 mM $CaCl_2$ and 20% KSR, for example.

ES cells can be generally selected by Real-Time PCR using alkaline phosphatase, the expression of a gene marker such as Oct-3/4, Nanog, or the like as an index. In particular, for selection of human ES cells, the expression of a gene marker such as OCT-3/4, NANOG, or ECAD can be used as an index (E. Kroon et al. (2008), Nat. Biotechnol., 26: 443-452).

Human ES cell lines, such as WA01 (HI) and WA09 (H9) are available from WiCell Research Institute. Human ES cell lines, such as KhES-1, KhES-2, and KhES-3 are available from the Institute for Frontier Medical Sciences, Kyoto University (Kyoto, Japan).

(B) Spermatogonial Stem Cells

Spermatogonial stem cells are testis-derived pluripotent stem cells, serving as an origin for spermatogenesis. Spermatogonial stem cells can also be induced to differentiate into cells of various lines in a manner similar to that in ES cells. For example, the cells have properties such that a chimeric mouse can be produced when transplanted into mouse blastocysts (M. Kanatsu-Shinohara et al. (2003) Biol. Reprod., 69: 612-616; K. Shinohara et al. (2004), Cell, 119: 1001-1012). Spermatogonial stem cells are self-replicable in a culture solution containing a glial cell line-derived neurotrophic factor (GDNF) or spermatogonial stem cells can be obtained by repeated subculture of the cells under culture conditions similar to those for ES cells (Masanori Takebayashi et al., (2008), Experimental Medicine, Vol. 26, No. 5 (Extra Number), pp. 41-46, YODOSHA (Tokyo, Japan)).

(C) Embryonic Germ Cells

Embryonic germ cells are cells established from primordial germ cells at the prenatal period and have pluripotency similar to that of ES cells. Embryonic germ cells can be established by culturing primordial germ cells in the presence of substances such as LIF, bFGF, and a stem cell factor (Y. Matsui et al. (1992), Cell, 70: 841-847; J. L. Resnick et al. (1992), Nature, 359: 550-551).

(D) Induced Pluripotent Stem Cells

Induced pluripotent stem (iPS) cells can be prepared by introducing a specific reprogramming factor in the form of DNA or protein into somatic cells. iPS cells are somatic cell-derived artificial stem cells having properties almost equivalent to those of ES cells, such as pluripotency and proliferation potency via self-replication (K. Takahashi and S. Yamanaka (2006) Cell, 126: 663-676; K. Takahashi et al. (2007) Cell, 131: 861-872; J. Yu et al. (2007) Science, 318: 1917-1920; Nakagawa M et al., Nat. Biotechnol., 26 (2008): 101-106; WO 2007/069666). A reprogramming factor may be composed of a gene specifically expressed in ES cells, a gene product or non-cording RNA thereof, or a gene playing an important role in maintenance of undifferentiation of ES cells, a gene product or non-cording RNA thereof, or a low molecular weight compound. Examples of a gene to be contained in such a reprogramming factor include Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sall1, Sall4, Esrrb, Nr5a2, Tbx3, and Glis1. These reprogramming factors may be used independently or in combination. Examples of such a combination of reprogramming factors include those described in WO2007/069666, WO2008/118820, WO2009/007852, WO2009/032194, WO2009/058413, WO2009/057831, WO2009/075119, WO2009/079007, WO2009/091659, WO2009/101084, WO2009/101407, WO2009/102983, WO2009/114949, WO2009/117439, WO2009/126250, WO2009/126251, WO2009/126655, WO2009/157593, WO2010/009015, WO2010/033906, WO2010/033920, WO2010/042800, WO2010/050626, WO2010/056831, WO2010/068955, WO2010/098419, WO2010/102267, WO2010/111409, WO2010/111422, WO2010/115050, WO2010/124290. WO2010/147395, WO2010/147612, Huangfu D, et al. (2008), Nat. Biotechnol., 26: 795-797, Shi Y, et al. (2008). Cell Stem Cell, 2: 525-528, Eminli S, et al. (2008), Stem Cells. 26: 2467-2474, Huangfu D, et al. (2008), Nat Biotechnol. 26: 1269-1275, Shi Y, et al. (2008), Cell Stem Cell, 3, 568-574, Zhao Y, et al. (2008), Cell Stem Cell, 3: 475-479, Marson A, (2008), Cell Stem Cell, 3, 132-135, Feng B, et al. (2009), Nat Cell Biol. 11: 197-203, R. L. Judson et al., (2009), Nat. Biotechnol., 27: 459-461, Lyssiotis C A, et al. (2009), Proc Natl Acad Sci U.S.A., 106: 8912-8917, Kim J B, et al., (2009), Nature. 461: 649-643, Ichida J K, et al., (2009), Cell Stem Cell. 5: 491-503, Heng J C, et al. (2010), Cell Stem Cell. 6:167-74, Han J, et al. (2010), Nature. 463:1096-100, Mali P, et al. (2010), Stem Cells. 28: 713-720, Maekawa M, et al. (2011), Nature. 474: 225-9.

Examples of the above reprogramming factors include factors to be used for enhancing the establishment efficiency, such as histone deacetylase (HDAC) inhibitors [for example, low-molecular-weight inhibitors such as valproic acid (VPA), trichostatin A, sodium butyrate, MC 1293, and M344, and nucleic acid expression inhibitors such as siRNA and shRNA against HDAC (e.g., HDAC1 siRNA Smartpool® (Millipore), and HuSH 29mer shRNA Constructs against HDAC1 (OriGene))], MEK inhibitors (for example, PD184352, PD98059, U0126, SL327 and PD0325901), Glycogen synthase kinase-3 inhibitors (for example, Bio and CHIR99021), DNA methyltransferase inhibitors (for example, 5-azacytidine), histone methyltransferase inhibitors (for example, low molecular weight inhibitors such as BIX-01294, and nucleic acid expression inhibitors such as siRNA and shRNA against Suv39h1, Suv39h2, SetDB1 and G9a), L-channel calcium agonists (for example, Bayk8644), butyric acid, TGFβ inhibitors or ALK5 inhibitors (for example, LY364947, SB431542, 616453, and A-83-01), p53 inhibitors (for example, siRNA and shRNA against p53), ARID3A inhibitors (for example, siRNA and shRNA against ARID3A), miRNA such as miR-291-3p, miR-294, miR-295 and mir-302, Wnt Signaling (for example, soluble Wnt3a), nerve peptide Y, prostaglandins (for example, prostaglandin E2, and prostaglandin J2), hTERT, SV40LT, UTF1, IRX6, GLIS1, PITX2, and DMRTB1. In the description, these factors to be used for improvement of establishment efficiency are not especially differentiated from reprogramming factors.

These reprogramming factors may be introduced in the form of protein into somatic cells by a technique such as lipofection, binding with a cell membrane-permeable peptide (e.g., HIV-derived TAT and polyarginine), or microinjection.

Meanwhile, in the form of DNA, for example, these reprogramming factors can be introduced into somatic cells by a technique using a vector such as a virus, a plasmid, or an artificial chromosome, lipofection, liposome, microinjection, or the like. Examples of a viral vector include a retrovirus vector, a lentivirus vector (these are according to Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a Sendai virus vector (WO 2010/008054). Moreover, examples of an artificial chromosome vector include a human artificial chromosome (HAC), a yeast artificial chromosome (YAC), and a bacterial artificial chromosome (BAC, PAC). As a plasmid, a plasmid for mammalian cells can be used (Science, 322: 949-953, 2008). A vector can contain regulatory sequences such as a promoter, an enhancer, a ribosome binding sequence, a terminator, and a polyadenylation site, so that a nuclear reprogramming substance can be expressed. The above vector may further contain, if necessary, a selection marker sequence such as a drug resistance gene (e.g., a kanamycin resistance gene, an ampicillin resistance gene, and a puromycin resistance gene), a thymidine kinase gene, and a diphtheria toxin gene, and a reporter gene sequence such as a green fluorescent protein (GFP), β glucuronidase (GUS), and FLAG. Also, in order to cleave both a gene encoding a reprogramming factor or a promoter and a gene encoding a reprogramming factor binding thereto after introduction into somatic cells, the above vector may have LoxP sequences located before and after the relevant portion.

Furthermore, in the form of RNA, the reprogramming factor may be introduced into somatic cells by a technique such as lipofection or microinjection. In order to suppress degradation, RNA caused to incorporate 5-methylcytidine and pseudouridine (TriLink Biotechnologies) can also be used herein (Warren L, (2010) Cell Stem Cell. 7: 618-630).

Examples of a culture solution for inducing iPS cells include DMEM, DMEM/F12, and a DME culture solution containing 10-15% FBS (these culture solutions may further appropriately contain LIF, penicillin/streptomycin, puromycin, L-glutamine, nonessential amino acids, β-mercaptoethanol, and the like), or commercially available culture solutions [e.g., a culture solution for culturing mouse ES cells (TX-WES culture solution, Thromb-X), a culture solution for culturing primate ES cells (culture solution for primates ES/iPS cells, ReproCELL), and a serum free medium (mTeSR, Stemcell Technology)].

An example of culture methods is as follows. Somatic cells are brought into contact with reprogramming factors on a DMEM or DMEM/F12 culture solution containing 10% FBS at 37° C. in the presence of 5% $CO_2$ and are cultured for about 4 to 7 days. Subsequently, the cells are reseeded on feeder cells (e.g., mitomycin C-treated STO cells or SNL cells). About 10 days after contact between the somatic cells and the reprogramming factors, cells are cultured in a bFGF-containing culture solution for culturing primate ES cells. About 30-45 days or more after the contact, iPS cell-like colonies can be formed.

Alternatively, cells may be cultured in a 10% FBS-containing DMEM culture solution (the solution may further appropriately contain LIF, penicillin/streptomycin, puromycin, L-glutamine, nonessential amino acids, β-mercaptoethanol, or the like) on feeder cells (e.g., mitomycin C-treated STO cells, and SNL cells) in the presence of 5% $CO_2$ at 37° C. About 25-30 days or more after culturing, ES cell-like colonies can be formed. Desirable examples of a method to be employed herein include a method using somatic cells (to be reprogrammed) themselves instead of feeder cells (Takahashi K, et al. (2009), PLoS One. 4: e8067 or WO2010/137746) and a method using extracellular matrix (e.g., Laminin-5 (WO2009/123349) and matrigel (BD)) instead of feeder cells.

Another example of such a method is a method that involves culturing with the use of a serum-free medium (Sun N, et al. (2009), Proc Natl Acad Sci U.S.A. 106: 15720-15725). Moreover, in order to increase establishment efficiency, iPS cells may be established under hypoxic conditions (oxygen concentration of 0.1% or more and 15% or less) (Yoshida Y, et al. (2009), Cell Stem Cell. 5: 237-241 or WO2010/013845).

During the above culture, culture solution exchange with a fresh culture solution is performed once a day from day 2 after the start of culture. In addition, the number of somatic cells to be used for nuclear reprogramming is not limited, but ranges from about $5 \times 10^3$ to about $5 \times 10^6$ cells per culture dish (100 $cm^2$).

iPS cells can be selected based on the shape of colonies formed. Meanwhile, when a drug resistance gene that is expressed in conjunction with a gene (e.g., Oct3/4, and Nanog) is expressed upon reprogramming of somatic cells is introduced as a marker gene, the thus established iPS cells can be selected by culturing cells in a culture solution (selective culture solution) containing the drug corresponding thereto. Also, when a marker gene is a fluorescent protein gene, iPS cells can be selected by fluorescent microscopic observation. When a marker gene is a luminescent enzyme, iPS cells can be selected by adding a luminescent substrate.

The term "somatic cells" as used herein refers to all animal cells (preferably, cells of mammals including humans) excluding germ-line cells such as sperm cells, spermatocytes, ova, oocytes, and ES cells or totipotent cells. Examples of somatic cells include, but are not limited to, fetal somatic cells, neonate somatic cells, and mature healthy or pathogenic somatic cells, as well as primary cultured cells, passaged cells, and established cell lines. Specific examples of somatic cells include (1) tissue stem cells (somatic stem cells) such as neural stem cells, hematopoietic stem cells, mesenchymal stem cells, and dental pulp stem cells (2) tissue precursor cells, and (3) differentiated cells such as lymphocytes, epithelial cells, endothelial cells, muscle cells, fibroblasts (e.g., skin cells), hair cells, hepatocytes, gastric mucosal cells, enterocytes, splenocytes, pancreatic cells (e.g., exocrine pancreatic cells), brain cells, pneumocytes, renal cells and fat cells.

Moreover, when iPS cells are used as materials for cells for transplantation, the use of somatic cells, the HLA genotype of which is the same as or substantially the same as that of a recipient (an individual to which the somatic cells are transplanted) is desired from the viewpoint of causing no rejection. Here, the term "substantially the same" means that the HLA genotypes match to the extent that the immunoreaction to the transplanted cells can be suppressed using an immunosuppressive agent. Examples of such somatic cells include somatic cells having an HLA genotype wherein 3 gene loci (HLA-A, HLA-B and HLA-DR) or 4 gene loci (HLA-C in addition to the aforementioned 3 gene loci) are identical to those of the recipient.

(E) ES Cells Derived from Clone Embryo Obtained by Nuclear Transplantation ntES cells are ES cells derived from clone embryo prepared by nuclear transplantation techniques, having properties almost the same as those of fertilized egg-derived ES cells (T. Wakayama et al., (2001), Science, 292: 740-743; S. Wakayama et al. (2005), Biol. Reprod., 72: 932-936; J. Byrne et al. (2007), Nature, 450: 497-502). Specifically, ntES (nuclear transfer ES) cells are established from the inner cell mass of a blastocyst from a clone embryo that is obtained via substitution of the nucleus of an unfertilized egg with the nucleus of a somatic cell. For preparation of ntES cells, nuclear transplantation techniques (J. B. Cibelli et al. (1998), Nature Biotechnol., 16: 642-646) and the above ES cell preparation techniques are used in combination (Kiyoka Wakayama et al., (2008), Experimental Medicine, Vol. 26, No. 5 (Extra Number), pp. 47-52). Upon nuclear transplantation, the nucleus of a somatic cell is injected into a mammalian enucleated unfertilized egg and then the resultant is cultured for several hours, so that reprogramming can be carried out.

(F) Multilineage-Differentiating Stress Enduring Cells (Muse Cells)

Muse cells are pluripotent stem cells that are produced by the method described in WO2011/007900. Specifically, Muse cells are pluripotent cells that can be obtained by treating fibroblasts or bone marrow stromal cells with trypsin for a long period of time and preferably for 8 hours or 16 hours, and then performing suspension culture. Muse cells are positive for SSEA-3 and CD105.

<Method for Inducing Differentiation of Pluripotent Stem Cells into Pancreatic Precursor Cells>

In the present invention, the differentiation of pluripotent stem cells into pancreatic precursor cells can be induced by any method known by persons skilled in the art. Examples thereof include, but are not particularly limited to, a method using activin A (JP Patent Application No. 2008-40781), a method that involves applying weak pulse current and heat (JP Patent Application No. 2010-153907), a method that involves performing co-culture with M15 cells (WO2006/126574), a multistep induction method that involves culturing cells in a medium containing activin A and Wnt3a, culturing in a medium containing FGF10 and KAAD-cyclopamine, and culturing in a medium containing FGF10, KAAD-cyclopamine, and retinoic acid (Chen S, et al., Nat Chem Biol. 2009, 5, 258-265), and an induction method that involves culturing in a medium containing activin A, and then culturing in a medium containing retinoic acid (Jiang W, et al., Cell Res. 2007, 17, 333-344.). Preferably, in the present invention, upon induction of the differentiation of pluripotent stem cells into pancreatic precursor cells, a method that involves the following 4 steps can be employed:

(i) a step of culturing pluripotent stem cells such as human induced pluripotent stem cells in a medium containing Activin A and GSK-3β (Glycogen Synthase Kinase 3β) inhibitor ($1^{st}$ step);

(ii) a step of culturing the cells obtained in step (i) in a culture solution supplemented with FGF10 and Smoothened (SMO) inhibitor ($2^{nd}$ step);

(iii) a step of culturing the cells obtained in step (ii) in a culture solution supplemented with retinoic acid, FGF10 and an SMO inhibitor (3$^{rd}$ step); and (iv) a step of culturing the cells obtained in step (iii) in a culture solution supplemented with protein kinase C activator and FGF10 (4$^{th}$ step).

(1$^{st}$ Step) Step of Culturing Pluripotent Stem Cells in a Medium Containing Activin A and a GSK-3β Inhibitor In this step, human pluripotent stem cells may be separated by an arbitrary method and then cultured by suspension culture or adhesion culture using a coated culture dish. As a culture method in the present invention, preferably adhesion culture is employed. Here, examples of a method for separating human pluripotent stem cells include a method for mechanical separation and a separation method using a separation solution having protease activity and collagenase activity (e.g., Accutase™ and Accumax™) or a separation solution having only collagenase activity. Preferably, a method that is employed herein involves: separating human pluripotent stem cells using a separation solution (particularly preferably, Accutase™) having protease activity and collagenase activity; and then mechanically finely dispersing cells into single cells. Human pluripotent stem cells to be used herein are preferably cultured to 80% confluency in the dish used herein so as to form colonies.

The term "suspension culture" refers to a culture of cells in a condition where cells do not adhere to a culture dish. Suspension culture can be carried out using a culture dish that has not been artificially treated (e.g., via a coating treatment using an extracellular matrix, or the like) in order to improve its ability to adhere to cells or treated (e.g., via a coating treatment using polyhydroxyethyl methacrylate (poly-HEMA)) to artificially suppress adhesion. However, the examples are not limited thereto.

Also, in adhesion culture, cells are cultured in an arbitrary medium in a coated culture dish. Examples of a coating agent include matrigel (BD), collagen, gelatin, laminin, heparan sulfate proteoglycan, entactin, and a combination thereof. A preferable example thereof is matrigel.

The medium to be used in this step can be prepared using a medium for culturing animal cells, as a basal medium. Examples of a basal medium include IMDM, Medium 199, Eagle's Minimum Essential Medium (EMEM), αMEM, Doulbecco's modified Eagle's Medium (DMEM), Ham's F12 medium, an RPMI 1640 medium, Fischer's medium, and mixtures thereof. Preferably, such a medium is an RPMI 1640 medium. A medium may contain serum or may be serum-free. If necessary, for example, a medium may contain one or more serum substitutes, such as albumin, transferrin, Knockout Serum Replacement (KSR) (a serum substitute for FBS upon culture of ES cells), N2 supplement (Invitrogen), B27 supplement (Invitrogen), a fatty acid, insulin, a collagen progenitor, a trace element, 2-mercaptoethanol, and 3'-thiolglycerol, as well as, one or more substances such as a lipid, an amino acid, L-glutamine, Glutamax (Invitrogen), a nonessential amino acid, a vitamin, a growth factor, a low molecular weight compound, an antibiotic, an antioxidant, a pyruvic acid, a buffering agent, and inorganic salts.

Examples of a growth factor include, but are not limited to, Wnt1, Wnt3, Wnt3a, Wnt4, Wnt7a, and Activin. In this step, at least Activin A is used as a growth factor.

The concentration of Activin A in a medium generally ranges from, but is not limited to, 1 ng/ml to 200 ng/ml, such as 1 ng/ml, 25 ng/ml, 50 ng/ml, 60 ng/ml, 70 ng/ml, 80 ng/ml, 90 ng/ml, 95 ng/ml, 100 ng/ml, 110 ng/ml, 120 ng/ml, 130 ng/ml, 140 ng/ml, 150 ng/ml, 160 ng/ml, 170 ng/ml, 180 ng/ml, 190 ng/ml, and 200 ng/ml. The concentration thereof is preferably 100 ng/ml.

Examples of a low molecular weight compound to be used in this step include, but are not limited to, a GSK-3β inhibitor and a ROCK (Rho dependent protein kinase) inhibitor. In this step, at least the GSK-3β inhibitor is used as a low molecular weight compound.

The term "GSK-3β inhibitor" is defined as a substance that inhibits the kinase activity (e.g., capacity to phosphorylate β catenin) of a GSK-3β protein. Many examples of the GSK-3β inhibitor have already been known, including BIO (another name, GSK-3β inhibitor IX; 6-bromoindirubin 3'-oxime) that is an indirubin derivative, SB216763 (3-(2, 4-dichlorophenyl)-4-(1-methyl-1H-indole-3-yl)-1H-pyrrole-2,5-dione) that is a maleimide derivative, GSK-3β inhibitor VII (4-dibromoacetophenone) that is a phenyl α bromomethylketone compound, L803-mts (another name, GSK-3β peptide inhibitor; Myr-N-GKEAPPAPPQSpP-NH$_2$) that is a cell membrane-permeable phosphorylated peptide, and CHIR99021 (6-[2-[4-(2,4-Dichlorophenyl)-5-(4-methyl-1H-imidazol-2-yl)pyrimidin-2-ylamino]ethylamino]pyridine-3-carbonitrile) having high selectivity. These compounds are commercially available from Calbiochem, Biomol, or the like and thus can be easily used. However, these compounds may also be obtained from another source or can be prepared.

A GSK-3β inhibitor to be used in the present invention can be preferably CHIR99021.

The concentration of CHIR99021 in a medium generally ranges from, but is not limited to, 1 nM to 50 μM, such as 1 nM, 10 nM, 50 nM, 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. Preferably, the concentration thereof is 1 μM.

Examples of the ROCK inhibitor are not particularly limited, as long as it can suppress the functions of Rho kinase (ROCK), and include Y-27632 (e.g., see Ishizaki et al., Mol. Pharmacol. 57, 976-983 (2000); Narumiya et al., Methods Enzymol. 325, 273-284 (2000)), Fasudil/HA1077 (e.g., see Uenata et al., Nature 389: 990-994 (1997)), H-1152 (e.g., see Sasaki et al., Pharmacol. Ther. 93: 225-232 (2002)), Wf-536 (e.g., see Nakajima et al., Cancer Chemother Pharmacol. 52(4): 319-324 (2003)) and derivatives thereof, as well as an antisense nucleic acid against ROCK, an RNA interference-inducing nucleic acid (e.g., siRNA), a dominant negative mutant, and expression vectors thereof. Also, as a ROCK inhibitor, another low molecular weight compound is known. In the present invention, such compounds and derivatives thereof can also be used (e.g., see U.S. Patent Application Publication Nos. 20050209261, 20050192304, 20040014755, 20040002508, 20040002507, 20030125344, 20030087919, and International Patent Publication WO02003/062227, WO2003/059913, WO2003/062225, WO2002/076976, and WO2004/039796). In the present invention, preferably, one, two or more types of ROCK inhibitor can be used.

A ROCK inhibitor to be used in the present invention can be preferably Y-27632 ((R)-(+)-trans-4-(1-aminoethyl)-N-(4-pyridyl)cyclohexanecarboxamide).

The concentration of Y-27632 generally ranges from, but is not limited to, 100 nM to 50 μM, such as 100 nM, 500 nM, 750 nM, 1 μM, 2 μM, 3 μM, 4 μM, 5 μM, 6 μM, 7 μM, 8 μM, 9 μM, 10 μM, 15 μM, 20 μM, 25 μM, 30 μM, 40 μM, and 50 μM. The concentration thereof is preferably 10 μM.

A substituent of a low molecular weight compound can be easily substituted by persons skilled in the art based on the common technical knowledge in the art and can be arbitrarily varied as long as the properties of the above compounds (e.g., a GSK-3β inhibitor and a ROCK inhibitor) can be retained.

A preferable example of a medium to be used in this step is a medium prepared by appropriately adding a ROCK inhibitor to a RPMI11640 medium containing B27, Penicillin/Streptomycin, Activin A and CHIR99021.

The temperature for culture ranges from about 30° C. to 40° C. and is preferably about 37° C., but the examples are not limited thereto. Culture is carried out under an air atmosphere containing $CO_2$. $CO_2$ concentration ranges from about 2% to 5% and is preferably 5%. The time for culture is at least 3 days, such as 3, 4, 5, 6, 7, 8, 9, 10, 11, and 12 days. The time for culture is preferably at least 4 days, more preferably 4 to 6 days.

($2^{nd}$ Step) Step of Culturing the Cells Obtained in the $1^{st}$ Step in a Culture Solution Supplemented with FGF10 and an SMO Inhibitor In this step, when the above $1^{st}$ step is adhesion culture, the thus obtained cells may be continuously cultured via medium exchange. Alternatively, when the above $1^{st}$ step is suspension culture, the thus obtained cell population may be directly cultured in an arbitrary medium in a coated culture dish. Examples of a coating agent include matrigel (BD), collagen, gelatin, laminin, heparan sulfate proteoglycan, entactin, and combinations thereof. A preferable example thereof is matrigel.

A medium to be used in this step can be prepared using a medium for culturing animal cells, as a basal medium. Examples of a basal medium include IMDM, Medium 199, Eagle's Minimum Essential Medium (EMEM), αMEM, Doulbecco's modified Eagle's Medium (DMEM), Ham's F12 medium, an RPMI 1640 medium, Fischer's medium, and mixtures thereof. Preferably, such a medium is DMEM. A medium may contain serum or may be serum-free. If necessary, for example, a medium may contain one or more serum substitutes, such as albumin, transferrin, sodium selenite, ITS-X (Invitrogen: containing insulin, transferrin, and sodium selenite), Knockout Serum Replacement (KSR) (a serum substitute of FBS for ES cell culture)), N2 supplement (Invitrogen), B27 supplement (Invitrogen), a fatty acid, insulin, a collagen precursor, a trace element, 2-mercaptoethanol, and 3'-thiolglycerol, as well as one or more substances such as a lipid, an amino acid, L-glutamine, Glutamax, a nonessential amino acid, a vitamin, a growth factor, a low molecular weight compound, an antibiotic, an antioxidant, a pyruvic acid, a buffering agent, and inorganic salts.

Examples of a preferable growth factor in this step include Wnt1, Wnt3, Wnt3a, Wnt4, Wnt7a, Activin and the FGF family (e.g., bFGF, FGF7 or FGF10). In this step, at least FGF10 is used as a growth factor.

The concentration of FGF10 in a medium generally ranges from, but is not limited to, 1 ng/ml to 200 ng/ml, such as 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 125 ng/ml, 150 ng/ml, 175 ng/ml, and 200 ng/ml. The concentration thereof is preferably 50 ng/ml.

An example of a low molecular weight compound to be used in this step is an SMO inhibitor or a ROCK (Rho dependent protein kinase) inhibitor, but is not limited thereto. In this step, at least the SMO inhibitor is used.

The term "SMO inhibitor" is defined as a substance that acts on SMO (7-transmembrane protein) to inhibit its signal transduction. Examples thereof include cyclopamine, 3-Keto-N-(aminoethyl-aminocaproyl-dihydro-cinnamoyl) (KAAD)-cyclopamine, CUR-61414, SANT-1,2,3,4, IPI-926, IPI-269609, GDC-0449 and NVP-LDE-225. The SMO inhibitor to be used in the present invention is preferably KAAD-cyclopamine.

The concentration of KAAD-cyclopamine in a medium generally ranges from, but is not limited to, 10 nM to 2.5 µM, such as 10 nM, 50 nM, 100 nM, 150 nM, 200 nM, 250 nM, 300 nM, 350 nM, 400 nM, 450 nM, 500 nM, 1 µM, 1.5 µM, 2 µM, and 2.5 µM. The concentration thereof is preferably 250 nM.

An example of a medium to be preferably used in this step is DMEM containing L-glutamine, B27, Penicillin/Streptomycin, KAAD-cyclopamine and FGF10.

The temperature for culture ranges from about 30° C. to 40° C. and is preferably about 37° C., but the examples are not limited thereto. Culture is carried out under an air atmosphere containing $CO_2$. $CO_2$ concentration ranges from about 2% to 5% and is preferably 5%. The time for culture is at least 1 day, such as 1, 2, 3, 4, and 5 days. The time for culture is preferably 1 day.

($3^{rd}$ Step) Step of Culturing the Cells Obtained in the $2^{nd}$ Step in a Culture Solution Supplemented with Retinoic Acid, FGF10, and an SMO Inhibitor In this step, the cells obtained by the above $2^{nd}$ step may be continuously cultured via medium exchange or may be separated and then cultured again by adhesion culture. Examples of a separation method include a method that involves mechanical separation, and a separation method using a separation solution (e.g., Accutase™ and Accumax™) having protease activity and collagenase activity or a separation solution having only collagenase activity.

Furthermore, in adhesion culture, cells are cultured in an arbitrary medium in a coated culture dish. Examples of a coating agent include matrigel (BD), collagen, gelatin, laminin, heparan sulfate proteoglycan, entactin, and combinations thereof.

A medium to be used in this step can be prepared using a medium for culturing animal cells, as a basal medium. Examples of a basal medium include IMDM, Medium 199, Eagle's Minimum Essential Medium (EMEM), αMEM, Dulbecco's modified Eagle's Medium (DMEM), Ham's F12 medium, an RPMI 1640 medium, Fischer's medium, and mixtures thereof. Preferably, such a medium is DMEM. A medium may contain serum or may be serum-free. If necessary, for example, a medium may contain one or more serum substitutes, such as albumin, transferrin, sodium selenite, ITS-X (Invitrogen: containing insulin, transferrin, and sodium selenite), Knockout Serum Replacement (KSR) (a serum substitute of FBS for ES cell culture), N2 supplement (Invitrogen), B27 supplement (Invitrogen), a fatty acid, insulin, a collagen precursor, a trace element, 2-mercaptoethanol, and 3'-thiolglycerol, as well as one or more substances such as a lipid, an amino acid, L-glutamine, Glutamax, a nonessential amino acid, a vitamin, a growth factor, a low molecular weight compound, an antibiotic, an antioxidant, a pyruvic acid, a buffering agent, and inorganic salts.

Examples of a growth factor to be preferably used in this step include Wnt1, Wnt3, Wnt3a, Wnt4, Wnt7a, Activin and the FGF family (e.g., bFGF, FGF7 or FGF10). In this step, at least FGF10 is used as a growth factor.

The concentration of FGF10 in a medium generally ranges from, but is not limited to, 1 ng/ml to 200 ng/ml, such as 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 125 ng/ml, 150 ng/ml, 175 ng/ml, and 200 ng/ml. The concentration thereof is preferably 50 ng/ml.

Examples of a low molecular weight compound to be used in this step include, but are not limited to, an SMO inhibitor and retinoic acid or a ROCK inhibitor. In this step, at least an SMO inhibitor and retinoic acid are used as low molecular weight compounds. As SMO inhibitors, the above compounds can be used.

When KAAD-cyclopamine is selected as an SMO inhibitor, the concentration thereof in a medium generally ranges from, but is not limited to, 10 nM to 2.5 µM, such as 10 nM, 50 nM, 100 nM, 150 nM, 200 nM, 250 nM, 300 nM, 350 nM, 400 nM, 450 nM, 500 nM, 1 µM, 1.5 µM, 2 µM, and 2.5 µM. The concentration thereof is preferably 250 nM.

Furthermore, the concentration of retinoic acid in a medium generally ranges from, but is not limited to, 100 nM to 20 µM, such as 100 nM, 200 nM, 300 nM, 400 nM, 500 nM, 1 µM, 1.5 µM, 2 µM, 2.5 µM, 3 µM, 4 µM, 5 µM, 10 µM, and 20 µM. The concentration thereof is preferably 2 µM.

An example of a medium to be preferably used in this step is DMEM containing L-glutamine, B27, Penicillin/Streptomycin, KAAD-cyclopamine, FGF10 and retinoic acid.

The temperature for culture ranges from about 30° C. to 40° C. and is preferably about 37° C., but the examples are not limited thereto. Culture is carried out under an air atmosphere containing $CO_2$. $CO_2$ concentration ranges from about 2% to 5% and is preferably 5%. The time for culture is at least 2 days, such as 2, 3, 4, 5 and 6 days. The time for culture is preferably 2 days.

($4^{th}$ Step) Step of Culturing the Cells Obtained in the $3^{rd}$ Step in a Culture Solution Supplemented with a Protein Kinase C Activator and FGF10

In this step, the cells obtained by the above $3^{rd}$ step may be continuously cultured via medium exchange or may be separated and then cultured again by adhesion culture. Examples of a separation method include a method that involves mechanical separation, and a separation method using a separation solution (e.g., Accutase™ and Accumax™) having protease activity and collagenase activity or a separation solution having only collagenase activity.

Furthermore, in adhesion culture, cells are cultured in an arbitrary medium in a coated culture dish. Examples of a coating agent include matrigel (BD), collagen, gelatin, laminin, heparan sulfate proteoglycan, entactin, and combinations thereof.

A medium to be used in this step can be prepared using a medium for culturing animal cells, as a basal medium. Examples of a basal medium include IMDM, Medium 199, Eagle's Minimum Essential Medium (EMEM), αMEM, Doulbecco's modified Eagle's Medium (DMEM), Ham's F12 medium, an RPMI 1640 medium, Fischer's medium, and mixtures thereof. Preferably, such a medium is DMEM. A medium may contain serum or may be serum-free. If necessary, for example, a medium may contain one or more serum substitutes, such as albumin, transferrin, sodium selenite, ITS-X (Invitrogen: containing insulin, transferrin, and sodium selenite), Knockout Serum Replacement (KSR) (a serum substitute of FBS for ES cell culture)), N2 supplement (Invitrogen), B27 supplement (Invitrogen), a fatty acid, insulin, a collagen precursor, a trace element, 2-mercaptoethanol, and 3'-thiolglycerol, as well as one or more substances such as a lipid, an amino acid, L-glutamine, Glutamax, a nonessential amino acid, a vitamin, a growth factor, a low molecular weight compound, an antibiotic, an antioxidant, a pyruvic acid, a buffering agent, and inorganic salts.

Examples of a growth factor to be preferably used in this step include Wnt1, Wnt3, Wnt3a, Wnt4, Wnt7a, Activin, and the FGF family (e.g., bFGF, FGF7 or FGF10). In this step, at least FGF10 is used as a growth factor.

The concentration of FGF10 in a medium generally ranges from, but is not limited to, 1 ng/ml to 200 ng/ml, such as 1 ng/ml, 5 ng/ml, 10 ng/ml, 20 ng/ml, 30 ng/ml, 40 ng/ml, 50 ng/ml, 60 ng/ml, 70 ng/ml, 80 ng/ml, 90 ng/ml, 100 ng/ml, 125 ng/ml, 150 ng/ml, 175 ng/ml, and 200 ng/ml. The concentration thereof is preferably 50 ng/ml.

An example of a low molecular weight compound to be used in this step is, but is not limited to, a protein kinase C activator or a ROCK inhibitor. In this step, at least a protein kinase C activator is used as a low molecular weight compound. As protein kinase C activators, the above compounds can be used.

When indolactam V is selected as a protein kinase C activator in this step, the concentration thereof to be added to the medium generally ranges from, but is not limited to, 30 nM to 3 µM, such as 30 nM, 40 nM, 50 nM, 60 nM, 70 nM, 80 nM, 90 nM, 100 nM, 150 nM, 200 nM, 250 nM, 300 nM, 350 nM, 400 nM, 450 nM, 500 nM, 600 nM, 700 nM, 800 nM, 900 nM, 1 µM, 2 µM, and 3 µM. The concentration thereof is preferably 300 nM.

An example of a medium to be preferably used in this step is DMEM containing L-glutamine, B27, Penicillin/Streptomycin, indolactam V and FGF10.

The temperature for culture ranges from about 30° C. to 40° C. and is preferably about 37° C., but the examples are not limited thereto. Culture is carried out under an air atmosphere containing $CO_2$. $CO_2$ concentration ranges from about 2% to 5% and is preferably 5%. The time for culture is at least 2 days, such as 2, 3, 4, 5, 6, 7 and 8 days. The time for culture is preferably 2 to 4 days.

<Exocrine Pancreatic Cells>

In the present invention, exocrine pancreatic cells can be purified using the exocrine pancreatic cells prepared by the above method for inducing differentiation as an index. Exocrine pancreatic cells are identified by staining with the use of AMY2A, AMY2B, or another arbitrary marker for exocrine pancreatic cells, for example, and thus can be purified by a method known by persons skilled in the art.

The thus obtained exocrine pancreatic cells can be used for screening for a therapeutic agent for chronic pancreatitis, for example.

<Kit for Inducing the Differentiation of Pancreatic Precursor Cells into Exocrine Pancreatic Cells>

The present invention provides a kit for inducing the differentiation of pancreatic precursor cells into exocrine pancreatic cells. This kit contains a histone deacetylase inhibitor and/or a ligand protein for a Notch signal, along with a protein kinase C activator. This kit may further contain a growth factor, a compound, a culture solution, a dissociation solution, and a coating agent for a culture dish, which are used for the above described differentiation induction. This kit may further contain documents or instructions describing procedures for inducing differentiation.

<Kit for Inducing the Differentiation of Pluripotent Stem Cells into Exocrine Pancreatic Cells>

The present invention provides a kit for inducing the differentiation of pluripotent stem cells into exocrine pancreatic cells. This kit may further contain, in addition to the above described kit for inducing the differentiation of pancreatic precursor cells into exocrine pancreatic cells, a growth factor, a compound, a culture solution, a dissociation solution (including a reagent for dispersing human pluripotent stem cells into single cells), and a coating agent for a culture dish, which are used for inducing the differentiation of pluripotent stem cells into pancreatic precursor cells. The kit may further preferably contain a GSK-3β inhibitor, activin A, FGF10 and an SMO inhibitor. This kit may further contain documents or instructions describing procedures for inducing differentiation.

EXAMPLES

Example 1

Human ES cells (KhES3) received from Kyoto University (Kyoto, Japan) were cultured by a conventional method (Mori H, et al., Biochem Biophys Res Commun. 2006, 345, 926-932). ES cells were cultured on 6-cm dishes to 80%-90% confluency, and then 1 mL of Accutase™ was added to disperse ES cells into single cells.

ES cells dispersed into single cells were induced to differentiate into exocrine pancreatic cells according to protocols shown in FIG. 1. Specifically, the following 5 steps were carried out.

(Stage 1) ES cells were suspended in a RPMI1640 medium containing 2% B27 and Penicillin/Streptomycin, and then seeded in a matrigel-coated 24-well plate at 250,000/well. 100 ng/ml, Activin A and 1 μM CHIR99021 were added to adjust the amount of the medium to be 0.5 mL/well, and then cells were cultured for 6 days.

(Stage 2-1) The medium was substituted with DMEM containing 50 ng/ml FGF10, 0.25 μM KAAD (3-Keto-N-(aminoethyl-aminocaproyl-dihydro-cinnamoyl))-cyclopamine, 1% L-Glutamin, 2% B27, 50 mU/L Penicillin and 50 μg/L Streptomycin, and then cells were cultured for 1 day.

(Stage 2-2) The medium was substituted with DMEM containing 2 μM retinoic acid, 50 ng/ml FGF10, 0.25 μM KAAD-cyclopamine, 1% L-Glutamin, 2% B27, 50 mU/L Penicillin and 50 μg/L Streptomycin, and then cells were cultured for 2 days.

(Stage 2-3) The medium was substituted with DMEM containing 50 ng/ml FGF10, 300 nM (−)-indolactam V (ILV), 1% L-Glutamin, 2% B27, 50 mU/L Penicillin and 50 μg/L Streptomycin, and then cells were cultured for 4 days.

(Stage 3) The medium was substituted with DMEM containing 1 μM CHAP108 (formula 10), 300 nM ILV, 1% L-Glutamin, 2% B27, 50 mU/L Penicillin and 50 μg/L. Streptomycin, and then cells were cultured for 4 days or 8 days.

The cells obtained in each Stage were examined by PCR for the expression of each marker gene (SOX17, PDX1, and AMY2A). As a result, the expression of SOX17 and PDX1 was confirmed for the pancreatic precursor cells obtained in Stage 2, and the expression of all SOX17, PDX1, and AMY2A was confirmed for the exocrine pancreatic cells obtained in Stage 3 (FIG. 2).

Figure 3:
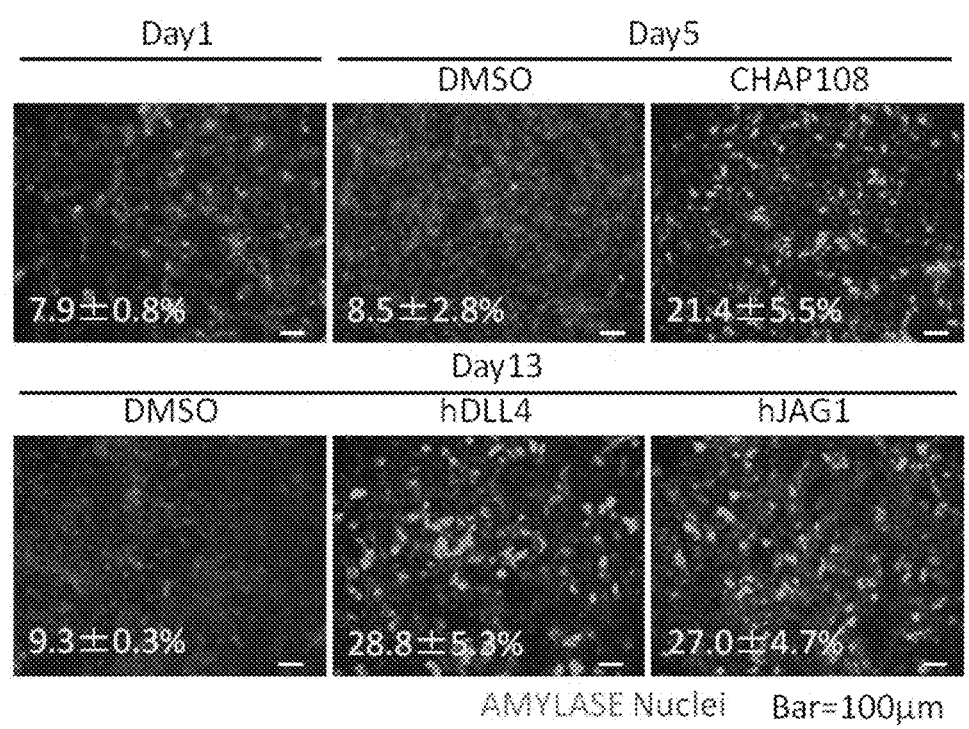
FIG. 3 shows the immunostaining images of exocrine pancreatic cells resulting from the induced differentiation of human ES cells.

The result obtained by culturing cells for 12 days in Stage 3 with the use of the ligand protein for a Notch signal, 0.5 mg/ml hDLL4 or 0.5 mg/ml hJAG1, instead of CHAP108 was compared with the result obtained by culturing cells for 4 days in Stage 3 with the use of CHAP108. The efficiencies for inducing exocrine pancreatic cells in the cases of CHAP108 (4 days), the same of hDLL4 (12 days), and the same of hJAG1 (12 days) were 21.4%, 28.8%, and 27.0%, respectively (FIG. 3). These values were significantly higher than the result obtained by adding DMSO as a negative control.

As described above, it was confirmed that exocrine pancreatic cells can be induced from PDX1-positive pancreatic precursor cells with the use of CHAP108, in a manner similar to the use of a ligand protein for a Notch signal.

Example 2

ES cells (KhES3) dispersed into single cells were induced to differentiate into exocrine pancreatic cells according to modified protocols shown in FIG. 1. Specifically, the following 5 steps were carried out.

(Stage 1) ES cells were suspended in a RPMI1640 medium containing 2% B27 and Penicillin/Streptomycin, and then seeded in a matrigel-coated 24-well plate at 250,000/well. 100 ng/mL Activin A and 1 μM CHIR99021 were added to adjust the amount of the medium to be 0.5 mL/well, and then cells were cultured for 4 days.

(Stage 2-1) The medium was substituted with DMEM containing 50 ng/ml FGF100, 0.25 μM KAAD (3-Keto-N-(aminoethyl-aminocaproyl-dihydro-cinnamoyl))-cyclopamine, 1% L-Glutamin, 2% B27, 50 mU/L Penicillin and 50 μg/L Streptomycin, and then cells were cultured for 1 day.

(Stage 2-2) The medium was substituted with DMEM containing 2 μM retinoic acid, 50 ng/ml FGF10, 0.25 μM KAAD-cyclopamine, 1% L-Glutamin, 2% B27, 50 mU/L Penicillin and 50 g/L Streptomycin, and then cells were cultured for 2 days.

(Stage 2-3) The medium was substituted with DMEM containing 50 ng/ml FGF10, 300 nM (−)-indolactam V (ILV), 1% L-Glutamin, 2% B27, 50 mU/L Penicillin and 50 μg/L Streptomycin, and then cells were cultured for 2 days.

(Stage 3) The medium was substituted with DMEM containing 1 μM CHAP108 (formula 10), 300 nM ILV, 1% L-Glutamin, 2% B27, 50 mU/L Penicillin and 50 μg/L Streptomycin, and then cells were cultured for 2 days.

Figure 4:
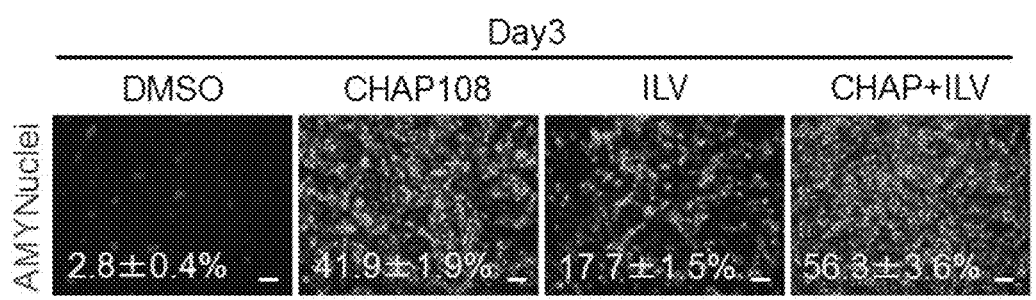
FIG. 4 shows the immunostaining images of exocrine pancreatic cells resulting from the induced differentiation of human ES cells.

The cells obtained after Stage 3 were examined by immunostaining with anti-Amylase. As a result, the Amylase positive rate in the case of using CHAP108 was 56.3% (FIG. 4). This rate was higher than that in the case of using DMSO as negative control (2.8%). For this result, present protocol as using CHAP108 is useful for inducing exocrine pancreatic cells from PDX1-positive pancreatic precursor cells.

The invention claimed is:

1. A method for producing exocrine pancreatic cells from PDX1-positive pancreatic precursor cells, comprising a step of
culturing PDX1-positive pancreatic precursor cells in a culture solution supplemented with a histone deacetylase inhibitor or a ligand protein for a Notch signal receptor, and a protein kinase C activator.

2. The method according to claim 1, wherein the histone deacetylase inhibitor is a compound having the structure of formula 1

25

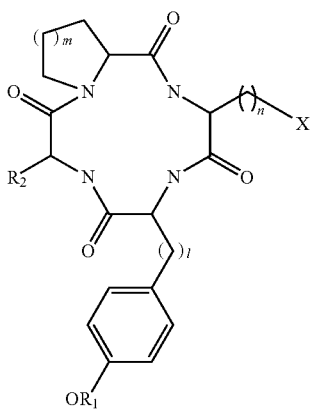

wherein, "l" represents 1 to 6, "m" represents 1 or 2, "n" represents 4 to 6, $R_1$ represents a $C_{1-6}$ alkyl group, $R_2$ represents a $C_{1-6}$ alkyl group, and X represents a substituent selected from the group consisting of (formula 1)

(formula 2)
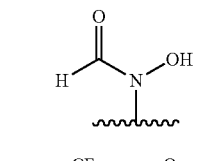

(formula 3)
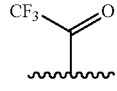

(formula 4)
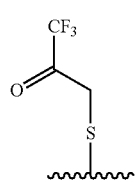

(formula 5)
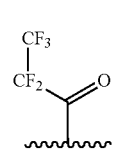

(formula 6)
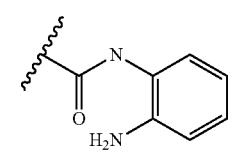

(formula 7)
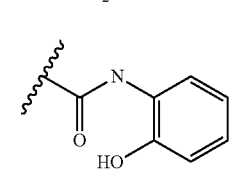

(formula 8)
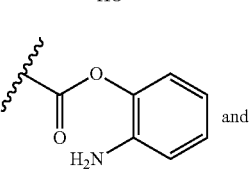
and (formula 9)
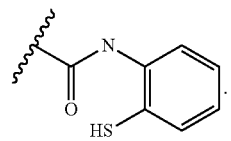

3. The method according to claim 1, wherein the histone deacetylase inhibitor is a compound having the following structure of formula 10

(formula 10)
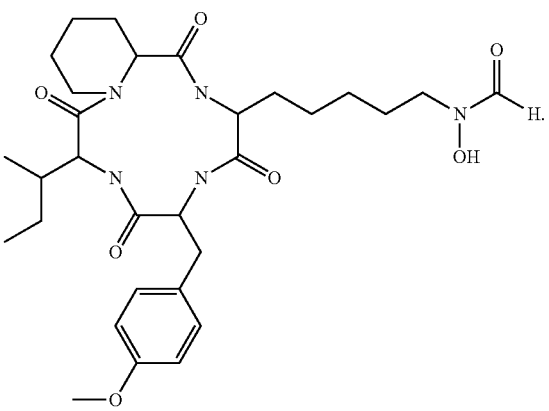

4. The method according to claim 1, wherein the ligand protein for the Notch signal receptor is DLL4 or JAG1.

5. The method according to claim 1, wherein the protein kinase C activator is indolactam V.

6. The method according to claim 1, wherein the step of culturing is performed for at least 2 days.

7. The method according to claim 1, wherein the PDX1-positive pancreatic precursor cells are PDX1-positive pancreatic precursor cells induced by the following steps (i) to (iv) from pluripotent stem cells:
 (i) culturing pluripotent stem cells in a culture solution supplemented with a GSK-3β inhibitor and activin A;
 (ii) culturing the cells obtained in (i) in a culture solution supplemented with FGF10 and an SMO inhibitor;
 (iii) culturing the cells obtained in (ii) in a culture solution supplemented with retinoic acid, FGF10, and an SMO inhibitor; and
 (iv) culturing cells obtained in (iii) in a culture solution supplemented with a protein kinase C activator and FGF10.

8. The method according to claim 7, wherein the GSK-3β inhibitor is CHIR99021.

9. The method according to claim 7, wherein the SMO inhibitor is KAAD-cyclopamine.

10. The method according to claim 7, wherein the protein kinase C activator is indolactam V.

11. The method according to claim 7, wherein step (i) comprises dispersing pluripotent stem cells into single cells.

12. The method according to claim 7, wherein step (i) of culturing is performed for at least 4 days.

13. The method according to claim 7, wherein step (ii) of culturing is performed for at least 1 day.

14. The method according to claim 7, wherein step (iii) of culturing is performed for at least 2 days.

15. The method according to claim 7, wherein step (iv) of culturing is performed for at least 2 days.

16. The method according to claim 1, wherein the PDX1-positive pancreatic precursor cells are PDX1-positive human pancreatic precursor cells.

17. A method for producing exocrine pancreatic cells from PDX1-positive pancreatic precursor cells, comprising a step of
culturing PDX1-positive pancreatic precursor cells in a culture solution supplemented with a histone deacetylase inhibitor and a ligand protein for a Notch signal receptor, and a protein kinase C activator.

18. A kit for producing exocrine pancreatic cells from PDX1-positive pancreatic precursor cells, comprising
a histone deacetylase inhibitor and a ligand protein for a Notch signal receptor, and a protein kinase C activator.

19. The kit according to claim 18, wherein the histone deacetylase inhibitor is a compound having the structure of formula 11

(formula 11)

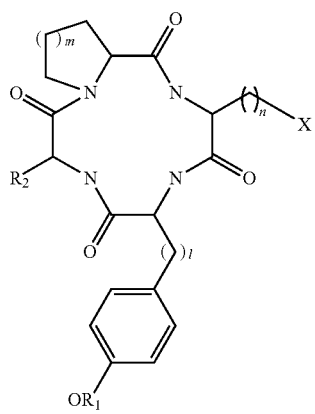

wherein, "l" represents 1 to 6, "m" represents 1 or 2, "n" represents 4 to 6, $R_1$ represents a $C_{1-6}$ alkyl group, $R_2$ represents a $C_{1-6}$ alkyl group, and X represents a substituent selected from the group consisting of (formula 12)

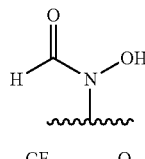

(formula 13)

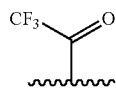

(formula 14)

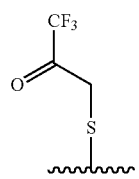

(formula 15)

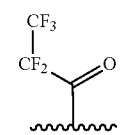

(formula 16)

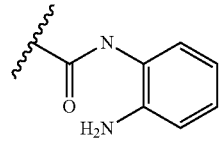

(formula 17)

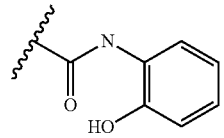

(formula 18)

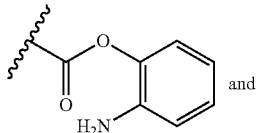

and (formula 19)

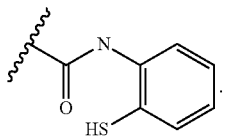

20. The kit according to claim 18, wherein the histone deacetylase inhibitor is a compound having the structure represented by the following formula 20

(formula 20)

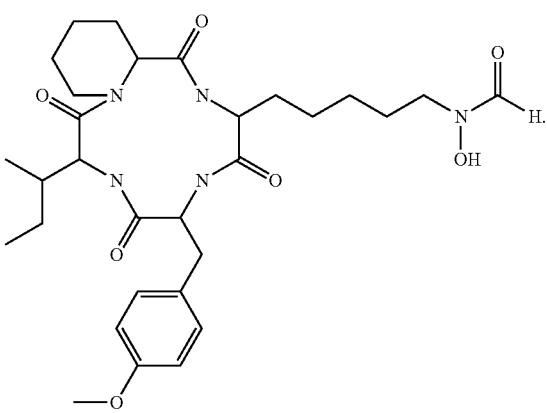

21. The kit according to claim 18, wherein the ligand protein for the Notch signal receptor is DLL4 or JAG1.

22. The kit according to claim 18, wherein the protein kinase C activator is indolactam V.

23. The kit according to claim 18, for producing exocrine pancreatic cells from pluripotent stem cells, further comprising a GSK-3β inhibitor, activin A, FGF10, and an SMO inhibitor.

24. The kit according to claim 23, wherein the GSK-3β inhibitor is CHIR99021.

25. The kit according to claim 23, wherein the SMO inhibitor is KAAD-cyclopamine.

* * * * *